(12) United States Patent
Li et al.

(10) Patent No.: US 6,210,969 B1
(45) Date of Patent: Apr. 3, 2001

(54) COMPOSITION AND METHOD FOR DIFFERENTIATION OF BASOPHIL AND EOSINOPHIL SUBPOPULATIONS OF LEUKOCYTES IN BLOOD

(75) Inventors: Yi Li; Jing Li, both of Miami, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/300,863

(22) Filed: Apr. 28, 1999

(51) Int. Cl.$^7$ ...................................................... G01N 31/00
(52) U.S. Cl. .................................. 436/10; 436/8; 436/17; 436/63; 436/164; 436/166; 436/174; 436/175; 252/408.1; 435/2
(58) Field of Search ................................. 436/8, 10, 17, 436/18, 63, 164, 166, 174, 175; 435/2; 252/408.1

(56) References Cited

U.S. PATENT DOCUMENTS

| | | | |
|---|---|---|---|
| 4,485,175 | 11/1984 | Ledis et al. | 436/63 |
| 4,528,274 * | 7/1985 | Carter et al. | 436/10 |
| 5,116,539 | 5/1992 | Hamaguchi et al. | 252/408.1 |
| 5,155,044 | 10/1992 | Ledis et al. | 436/17 |
| 5,180,677 * | 1/1993 | Di Ianni et al. | 436/17 |
| 5,196,346 | 3/1993 | Lefevre et al. | 436/63 |
| 5,242,832 * | 9/1993 | Sakata | 436/17 |
| 5,250,437 * | 10/1993 | Toda et al. | 436/10 |
| 5,389,549 | 2/1995 | Hamaguchi et al. | 436/10 |
| 5,496,734 * | 3/1996 | Sakata | 436/63 |
| 5,510,267 * | 4/1996 | Marshall | 436/63 |
| 5,518,928 | 5/1996 | Cremins et al. | 436/40 |
| 5,538,893 | 7/1996 | Sakata et al. | 436/10 |
| 5,677,183 | 10/1997 | Takarada et al. | 436/10 |
| 5,686,308 * | 11/1997 | Li et al. | 436/63 |
| 5,747,343 * | 5/1998 | Tsuchiya et al. | 436/63 |
| 5,763,280 * | 6/1998 | Li et al. | 436/66 |
| 5,786,224 * | 7/1998 | Li et al. | 436/63 |
| 5,817,518 | 10/1998 | Li et al. | 436/63 |
| 5,821,128 | 10/1998 | Provost | 436/63 |
| 5,843,608 | 12/1998 | Li et al. | 436/63 |
| 5,882,934 * | 3/1999 | Li et al. | 436/66 |
| 6,004,816 * | 12/1999 | Mizukami et al. | 436/10 |

FOREIGN PATENT DOCUMENTS 3-20667 * 1/1991 (JP) .

* cited by examiner

Primary Examiner—Maureen M. Wallenhorst
(74) Attorney, Agent, or Firm—Mitchell E. Alter

(57) ABSTRACT

This invention relates to lytic reagents and methods of using the lytic reagents for automatically determining leukocyte subpopulations in blood. More specifically, the new lytic reagents selectively lyse red blood cells and certain leukocyte subpopulations, which enables the differentiation of at least one subpopulation of leukocytes. The lytic reagents contain a polyoxyethylene based surfactant, a quatemary ammonium salt and an acid. When used in combination with a second lytic reagent system, one is able to obtain at least a five part differential of leukocytes by impedance and light scatter measurements, by impedance and radio frequency measurements, or by radio frequency and light scatter measurements.

36 Claims, 3 Drawing Sheets

COMPOSITION AND METHOD FOR DIFFERENTIATION OF BASOPHIL AND EOSINOPHIL SUBPOPULATIONS OF LEUKOCYTES IN BLOOD

FIELD OF THE INVENTION

The present invention relates to lytic reagent compositions and methods for differentiating leukocyte subpopulations of blood samples by means of suitable electronic instruments.

BACKGROUND OF THE INVENTION

Analysis of leukocyte populations from blood samples is an integral and essential part of diagnostic procedures regarding a multiplicity of pathologies. Measurements of basophils and eosinophils that are subpopulations of leukocytes are important to the diagnosis of several diseases.

Traditional analysis of blood samples involves the smearing of a blood sample on a microscope slide, followed by a visual analysis of the slide. This approach is extremely time consuming as well as being subject to the interpretation of the individual analyzing the slide. These factors have led to the development of automated leukocyte analysis utilizing flow cytometry. An essential step in leukocyte analysis using automated hematology instruments is the lysis of the red blood cells. Thus far, various lytic reagents and automated methods have been developed for use with whole blood samples.

U.S. Pat. No. 4,485,175 (to Ledis et al.) describes a reagent system and method for performing differential leukocyte determinations into three subpopulations utilizing automated cell counting equipment. This reagent system contains a blood diluent and a lytic reagent. The lytic reagent comprises a mixture of quatemary ammonium surfactants. This reagent system differentiates the leukocytes into three subpopulations: lymphocytes, monocytes and granulocytes.

U.S. Pat. No. 5,155,044 (to Ledis et al.) discloses a reagent system and method for the rapid isolation and analysis of leukocytes from a whole blood sample and enables automated differentiation into five subpopulations using an automated hematology analyzer capable of impedance (DC), radio frequency (RF) and light scatter (LS) measurements. The reagent system is composed of an aqueous lytic reagent which comprises an acid, or a mixture of acid and saponin, and an aqueous salt quench solution. This method is rapid and provides a five part leukocyte differential of a whole blood sample in a single step measurement.

U.S. Pat. No. 5,786,224 (to Li et al.) discloses a lytic reagent system and a method for automated differentiation of leukocytes into five subpopulations using impedance, radio frequency and light scatter measurement devices. The lytic reagent system is composed of an aqueous lytic reagent which comprises a polyoxyethylene based nonionic surfactant, SDS and an acid, and a stabilizing reagent which comprises a hypertonic, alkaline reagent composition. The disclosed lytic reagent system differentiates leukocyte into five subpopulations using a single measurement when impedance, radio frequency and light scatter measurements are used.

However, if the above two lytic reagent systems are used on a hematology analyzer equipped with only impedance and light scatter measurement devices, the basophil subpopulations will not be adequately differentiated from lymphocyte subpopulations. If only impedance and radio frequency measurements are used for the blood analysis, eosinophils will not be differentiated from neutrophils due to a complete overlap of the two populations in DC vs. Opacity (a function of DC and RF) scattergram.

Another approach for differentiation of leukocytes into four or five subpopulations is to use multiple reagents and multiple measurements. Separate reagents are used for differentiating the specific subpopulations. Typically, a first lytic reagent, like the ones revealed in U.S. Pat. No. 5,116,539 (to Hamaguchi et al.) and U.S. Pat. No. 5,389,549 (to Hamaguchi et al.) are used to differentiate the leukocytes into three subpopulations (i.e., monocytes, lymphocytes and granulocytes) using impedance and radio frequency measurements.

Hamaguchi et al. (U.S. Pat. No. 5,389,549) discloses a lytic reagent for differentiating leukocytes into the above mentioned three subpopulations using impedance and radio frequency measurements. The lytic reagent consists essentially of a first cytolytic solution having pH of 1.5–5.0 and containing a surfactant in an amount effective to reduce erythrocyte ghosts for distinction from leukocytes without causing undesirable leukocyte damage, wherein the surfactant consists essentially of a polyoxyethylene based nonionic surfactant represented by the formula:

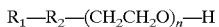

wherein $R_1$ is an alkyl, alkenyl or alkynyl group having 12 to 22 carbon atoms, $R_2$ is —O—, —$OC_6H_6$— or —COO—, and n is an integer of 20–100. The reagent further consists essentially of a second cytolytic solution used in combination with the first reagent. The second cytolytic solution has a pH of 5.0–12.0 and an osmolarity of 150–2000 mOsm/kg.

In U.S. Pat. No. 5,116,539, an additional lytic reagent is used with an additional measurement to obtain the eosinophil subpopulation. This enables a four part differentiation of lymphocytes, monocytes, eosinophils and the remaining granulocytes. The lytic reagent is composed of a polyoxyethylene-based nonionic surfactant and a buffer to adjust the pH of the solution within the range of 3–11. The lytic reagent lyses not only red blood cells but also the leukocytes except eosinophils so that the eosinophils can be counted based on their remaining cellular volume measured by DC. However, to achieve eosinophil separations the method of using the lytic reagent requires incubation of the sample mixture at 40° C. for a period of 50 seconds. This elevated temperature requirement necessitated instrumentation which is significantly more complex because the reactions must be thermostatically controlled. In addition, the extended reaction time directly decreases the throughput of the automated analyzer.

In U.S. Pat. No. 5,389,549, two additional lytic reagents are needed and two additional measurements are required to obtain the eosinophil and basophil subpopulations so as to provide a five part differential. More specifically, the additional lytic reagent for differential analysis of basophils is an aqueous solution composed of a polyoxyethylene-based nonionic surfactant, potassium ophthalate, hydrochloric acid and nitric acid. This lytic reagent lyses not only red blood cells but also the leukocytes except basophils so that the basophils can be counted based on their remaining cellular volume measured by DC. Again, to achieve basophil separation the method requires incubation of the sample mixture at elevated temperature. In this disclosure, the total eosinophil and basophil subpopulations obtained from separate measurements are subtracted from the total granulocyte population to obtain the neutrophil subpopulation.

Hamaguchi et al. teach that polyoxyethylene-based nonionic surfactants are moderate in lysing blood and is suitable for leukocyte differential analysis. Hamaguchi et al. further teach that quaternary ammonium salt damage cells violently and it is entirely meaningless to use a quaternary ammonium salt as a cytolytic agent in a method of classifying leukocytes by the combination of the impedance and radio frequency methods.

U.S. Pat. No. 5,196,346 (to Lefevre et al.) discloses a lytic reagent and method of using the same for automated determination of basophils in whole blood samples by lysing all blood cells, including both erythrocytes and leukocytes, with the exception of the basophils. The lytic reagent was composed of a polyoxyethylene ether-type surfactant, a phthalic acid/HCl mixture, sodium dodecyl sulfate (SDS) and a butylated hydroxytoluene-type antioxidizing agent. The disclosed method requires a thermostatically controlled reaction temperature between 30 to 40° C. and is limited to the counting of only basophils by impedance measurement.

U.S. Pat. No. 5,821,128 (to Provost) discloses lytic reagents and method for determination of basophils and eosinophils in whole blood samples. The lytic reagent for basophil measurement consists essentially of polyoxyethylene 9-lauryl ether and acids to maintain pH of the reagent between 2 and 3.5. The method uses the lytic reagent to lyse all blood cells including erythrocytes and leukocytes except basophils. Thereafter, the basophils are counted by impedance measurement. This method requires the lysing reaction to be performed at 40° C. Provost also discloses that by adjusting the pH of the lytic reagent to basic, i.e., between 9 and 10, the lytic reagent enables separation of eosinophils from other cell types by impedance measurement. Two separate reagents and measurements are required to provide basophil and eosinophil differentials.

U.S. Pat. No. 5,518,928 (to Cremins et al.) discloses a method of determination of basophils in whole blood samples by optical measurement. The method uses a non-cationic surfactant and an acid to lyse all blood cells, but retain basophils as intact cells. The lytic reagent contains a $C_6$–$C_{16}$ aliphatic alcohol ether of a polyoxyethylene glycol and has a pH about 1.8 to about 2.3. The method detects the light scattered by the cells and nucleus after treating a whole blood sample by the lytic reagent and differentiates basophils from other cell types.

Japanese Patent Publication No. Hei 3-20667 (Hamaguchi et al.) discloses a reagent for discriminately detecting leukocytes using impedance measurement. The reagent comprises a polyoxyethylene surfactant represented by the formula:

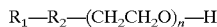

wherein $R_1$ is an alkyl, alkenyl or alkynyl group having 10 to 25 carbon atoms, $R_2$ is —O—, —$OC_6H_6$— or —COO—, and n is an integer of 12–30; and a quaternary ammonium salt represented by the formula:

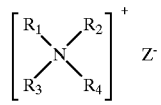

wherein $R_1$ is a $C_{10}$–$C_{20}$ alkyl group, each of $R_2$, $R_3$ and $R_4$ is $C_1$–$C_7$ alkyl groups and $Z^-$ is halogen atom; and having a pH between 3 and 4. Hamaguchi et al. teach that the sizes of basophils can be maintained at pH 3 or higher by using the reagent which is capable of making other leukocyte subpopulations naked.

U.S. Pat. No. 5,817,518 (to Li et al.) discloses a lytic reagent composition and a method for differentiating eosinophils using impedance and radio frequency measurements. The lytic reagent composition comprises an alkali metal salt of alkyl sulfate, an eosinolytic agent, a nonionic surfactant and a physiological salt. This lytic reagent composition lyses red blood cells and selectively affects and separates the eosinophil subpopulation from the other granulocyte subpopulations by selectively shrinking the eosinophils. Therefore, it enables the differentiation of eosinophils from other cell types when analyzed by impedance and radio frequency measurements. Moreover, Li et al. teaches a lytic reagent system and a method for automated differentiation of leukocytes into five subpopulations using impedance, radio frequency and light scatter measurement devices. The method comprises mixing a first aliquot blood sample with a first lytic reagent to lyse red blood cells and selectively shrink eosinophils, mixing a second aliquot blood sample with a second lytic reagent system to lyse red blood cells and preserve leukocytes, analyzing the treated sample of the first and second aliquots by impedance and radio frequency measurements to differentiate one and four leukocyte subpopulations, respectively; and reporting five leukocyte subpopulations.

U.S. Pat. No. 5,538,893 (to Sakata et al.) discloses a reagent and a method for classifying leukocytes into basophils, immature granulocytes, mononuclear cells and granulocytes other than basophils by measuring the size and a morphological feature of the cells. The reagent comprises at least one nonionic surfactant having an additional mole number of polyoxyethylene of 3 to 9, at least one cationic surfactant, a buffer adjusting a pH value to 2.5 to 4.0, and an alkali metal halide. The cationic surfactant is a pyridinium salt, or a quaternary ammonium salt having a formula:

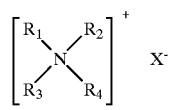

wherein $R_1$ is a $C_{10}$–$C_{18}$ alkyl or alkenyl group, each of $R_2$, $R_3$ and $R_4$ is $C_1$–$C_3$ alkyl or alkenyl groups and $X^-$ is halogen group. More specifically, the size is measured by forward low angle (1–5°) scattered light or impedance, and morphological features of the cells are measured by light side scattered or the light forward high angle (10–20°) scattered from a cell.

U.S. Pat. No. 5,677,183 (to Takarada et al.) discloses a method for classifying leukocytes into five subpopulations by using two separate lytic reagents. The first reagent enables a differentiation of leukocytes into four subpopulations, and the second reagent enables a differentiation of basophils from other cell types, when the treated sample is analyzed by the size and the morphological features of the cells. Takarada et al. teach that the second reagent is composed of polyoxyethylene (9) dodecyl ether, a quaternary ammonium salt and a buffer to adjust the pH to about 3.3. With this method, the cell size is measured by forward low angle (1–5°) scattered light or impedance, and morphological features of the cells are measured by light side scattered, or the light forward high angle (10–20°) scattered from a cell.

SUMMARY OF THE INVENTION

This invention relates to new lytic reagent compositions and methods for differentiation of leukocyte subpopulations.

In one embodiment, a lytic reagent composition enabling lysing red blood cells and selectively lysing leukocyte subpopulations is provided. The lytic reagent composition comprises a polyoxyethylene based surfactant, a $C_{14}$ quaternary ammonium salt, and an acid to adjust pH of the reagent composition from about 1.7 to about 2.4.

In another embodiment, a method and a lytic reagent system are provided for differentiating basophils from other cell types. The method comprises exposing a blood sample to the lytic reagent composition comprising a polyoxyethylene based surfactant, a $C_{14}$ quaternary ammonium salt and an acid for a time sufficient to lyse red blood cells and selectively lyse leukocyte subpopulations in the blood sample; adding a hypertonic alkaline stabilizing reagent composition to the exposed blood sample, wherein the stabilizing reagent composition inhibits further lytic action; and analyzing the blood sample to differentiate basophils from other cell types by impedance and light scatter measurements, or by radio frequency and light scatter measurements.

In a further embodiment, a method for differentiation of leukocytes into at least five subpopulations is provided. The method utilizes the first lytic reagent in combination with a second lytic reagent system to obtain at least a five part differential of leukocytes using impedance and light scatter measurements, or radio frequency and light scatter measurements.

Yet in another embodiment, a third lytic reagent composition and method for differential analysis of eosinophil subpopulation of the leukocytes are provided. The lytic reagent composition comprises a polyoxyethylene based surfactant, a $C_{16}$ quaternary ammonium salt, and an acid to adjust pH of the reagent composition from about 1.7 to about 2.3. The lytic reagent can further comprises a $C_{14}$ quaternary ammonium salt. The method comprises exposing a blood sample to the lytic reagent composition comprising a polyoxyethylene based surfactant, a $C_{16}$ quaternary ammonium salt, or a mixture of $C_{14}$ and $C_{16}$ quaternary ammonium salt, and an acid for a time sufficient to lyse red blood cells and selectively lyse leukocyte subpopulations in the blood sample;

adding a hypertonic alkaline stabilizing reagent composition to the exposed blood sample, wherein the stabilizing reagent composition inhibits further lytic action; and analyzing the blood sample to differentiate eosinophils from other cell types by one of the following measurements: (1) impedance and light scatter measurements, (2) impedance and radio frequency measurements, (3) radio frequency and light scatter measurements, (4) impedance measurement, or (5) radio frequency measurement.

In an additional embodiment, a method for differentiation of leukocytes into at least five subpopulations using impedance and radio frequency measurements is provided. The method utilizes a lytic reagent system comprising a lytic reagent composition that comprises a polyoxyethylene based surfactant, a mixture of $C_{16}$ and $C_{14}$ quaternary ammonium salt and an acid, and a hypertonic, alkaline stabilizing reagent composition, in combination with a second lytic reagent system to obtain at least a five part differential of leukocytes using impedance and radio frequency measurements.

DETAILED DESCRIPTION OF THE INVENTION

Figure 1A:
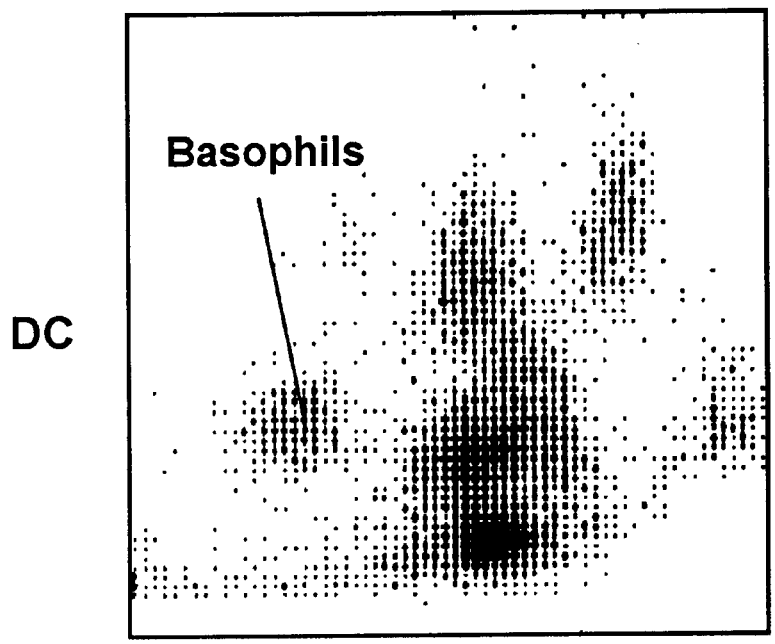
FIGS. 1a and 1b display a DC vs. rotated light scatter (RLS) diagram and a RF vs. Log LS diagram, respectively. The diagrams show basophil differentiation of a whole blood sample processed as described in Example I either using DC and light scatter measurements, or using RF and light scatter measurements.

The present invention relates to lytic reagent compositions and methods for the differentiation of leukocyte subpopulations by impedance (DC) and light scatter (LS) measurements, by impedance and radio frequency (RF) measurements, or by radio frequency and light scatter measurements. The lytic reagent compositions selectively lyse red blood cells and certain leukocyte subpopulations, while preserving other leukocyte subpopulations. More specifically, the lytic reagents and the methods of using the lytic reagents enable the differentiation of basophils and eosinophils using impedance and light scatter measurements, or radio frequency and light scatter measurements, enable the differentiation of eosinophils using impedance and radio frequency measurements, impedance or radio frequency measurement only. In addition, a method is provided for the differentiation of at least five leukocyte subpopulations using impedance and light scatter measurements, by impedance and radio frequency measurements, or by radio frequency and light scatter measurements.

In the first embodiment of the present invention, a first lytic reagent composition comprises:

(a) a polyoxyethylene based surfactant represented by the general formula:

wherein $R_1$ is an alkyl, alkenyl or alkynyl group having 10 to 22 carbon atoms, $R_2$ is —O— or —COO—, and n is between 20 and 35;

(b) a quaternary ammonium salt, represented by following molecular structure:

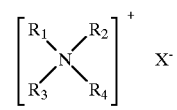

wherein $R_2$, $R_3$ and $R_4$ are alkyl groups having 1 to 4 carbon atoms and $X^-$ is chloride and bromide anions, $R_1$ is an alkyl, alkenyl or alkynyl group having 14 carbon atoms ($C_{14}$); and (c) an acid to adjust pH of the reagent composition from about 1.7 to about 2.4.

Preferably, $R_2$, $R_3$ and $R_4$ are methyl groups, and $R_1$ is a tetradecyl group. Optionally, the first lytic reagent composition can further comprise a second quaternary ammonium salt wherein $R_1$ is an alkyl, alkenyl or alkynyl group having 12 carbon atoms ($C_{12}$).

The polyoxyethylene based surfactant is known to have lytic function under acidic condition (U.S. Pat. No. 5,786, 224). It enables selective lysing of red blood cells and preserving leukocytes for differential analysis. However, in the presence of quaternary ammonium salt the first lytic reagent does not only lyse red blood cells, but also causes selective lysis of certain leukocyte subpopulations. The selectivity of the first lytic reagent toward certain leukocyte subpopulations depends on the chain length of the $R_1$ group of the quaternary ammonium salt. Tetradecyltrimethyl ammonium bromide, or a mixture of tetradecyltrimethyl ammonium bromide and dodecyltrimethyl ammonium chloride, causes lysis of monocytes, lymphocytes, and damage of neutrophils and eosinophils. However, basophils remain intact under the same condition. This selectivity provides separation of basophils from other cell types when analyzed by impedance and light scatter measurements, or radio frequency and light scatter measurements.

The concentration of the polyoxyethylene based surfactant is from about 0.05% to about 0.8% (W/V), preferably from 0.08% to 0.6% (W/V). When the concentration of the polyoxyethylene based surfactant is too high, it tends to protect all leukocytes from lysing. Consequently, the lytic reagent composition will be less selective toward different leukocyte subpopulations and resulting insufficient separation of basophils from other cell types.

The concentration of the quaternary ammonium salt is from about 0.15% to about 0.4% (W/V), preferably from about 0.2% to about 0.3% (W/V). When the concentration of the quaternary ammonium salt is too low, leukocytes other than basophils, particularly lymphocytes will not be lysed sufficiently so that the basophils can not be adequately separated from other leukocyte subpopulations. On the other hand, when the concentration of the quaternary ammonium salt is too high, basophils are also damaged by the lytic reagent.

For the purpose of the present invention, the acids can be an organic acid, an inorganic acid, or a mixture thereof. The examples of suitable acids in the lytic reagent composition are formic acid, citric acid, oxalic acid, malonic acid, phosphoric acid, and mixtures thereof.

The amount of the acid needs to be sufficient for lysing of red blood cells and leukocytes other than basophils. The concentration of the acid is from about 0.1% to about 0.3% (W/V). The pH of the lytic reagent is within a range from about 1.7 to about 2.4.

Optionally, additional additives can also be included in the lytic reagent composition in concentrations that their presence is compatible with the primary functional components of the lytic reagent composition. Among these additives are preservatives which have anti-oxidant properties, to increase the shelf-life of the composition, and which have anti-microbial properties. Preservatives that have anti-oxidant properties include but are not limited to EDTA and butylmethylphenol. Preservatives that have anti-microbial activity include but are. not limited to dimethyloldimethyl hydantoin and isothiozolone derivatives.

In a second embodiment of the present invention, a method and a lytic reagent system for differential analysis of basophils are provided. The method comprises the steps of: step 1) exposing a blood sample to a lytic reagent composition for a time sufficient to lyse red blood cells and leukocytes other than basophils, wherein the lytic reagent composition comprises:

(a) a polyoxyethylene based surfactant represented by the general formula:

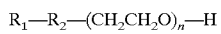

wherein $R_1$ is an alkyl, alkenyl or alkynyl group having 10 to 22 carbon atoms, $R_2$ is —O— or —COO—, and n is between 20 and 35;

(b) a quaternary ammonium salt, represented by following molecular structure:

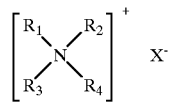

wherein $R_2$, $R_3$ and $R_4$ are alkyl groups having 1 to 4 carbon atoms and $X^-$ is chloride and bromide anions, $R_1$ is an alkyl, alkenyl or alkynyl group having 14 carbon atoms ($C_{14}$); and (c) an acid to adjust pH of the reagent composition from about 1.7 to about 2.4;

step 2) adding a hypertonic, alkaline stabilizing reagent composition to inhibit further lysing reaction; step 3) analyzing the treated blood sample to differentiate basophils from other cell types by impedance and light scatter measurements, or by radio frequency and light scatter measurements.

Preferably, $R_2$, $R_3$ and $R_4$ are methyl groups, and $R_1$ is a tetradecyl group. Optionally, the lytic reagent composition can further comprise a second quaternary ammonium salt wherein $R_1$ is an alkyl, alkenyl or alkynyl group having 12 carbon atoms ($C_{12}$). An example of a stabilizing reagent is provided in Example V.

The lytic reagent composition used in step 1 and the stabilizing reagent composition used in step 2 form a lytic reagent system for blood cell sample treatment, which enables the differentiation of basophils from other cell types by impedance and light scatter measurements, or by radio frequency and light scatter measurements.

The blood sample is exposed to the lytic reagent by mixing with the lytic reagent composition for a time sufficient to lyse red blood cells and leukocytes other than basophils in said blood sample. The blood sample is mixed with the lytic reagent composition at room temperature. Preferably the temperature will be between approximately 15 to 30° C. The mixing time is less than 10 seconds, preferably less than 5 seconds. After addition of the stabilizing reagent composition, the sample mixture is analyzed with an automated hematology instrument, which differentiates basophil subpopulation from other cell types.

The differential is performed using impedance (DC) and light scatter (LS) measurements, or using radio frequency (RF) and light scatter measurements with a focused flow cell. Details of the impedance, radio frequency and light scatter measurement principles and techniques are taught in U.S. Pat. Nos. 2,656,508, 4,298,836 and 5,125,737 assigned to Coulter Electronics, Inc.

Example I illustrates the application of a preferred embodiment of the disclosed lytic reagent composition for basophil differentiation of a whole blood sample. FIG. 1a shows the differential analysis of a whole blood sample processed as described in Example I using impedance and light scatter measurements. The cells flow through an aperture where impedance, radio frequency and light scatter measuring devices record the responses of the cells to the direct current, radio frequency, and incident light. The electrical and optical signals are processed and plotted as a two dimensional diagram, DC vs. rotated light scatter (RLS) illustrated in FIG. 1a. As shown, after exposure of a blood sample to the lytic reagent composition of the present invention, leukocytes other than basophils are damaged. Only basophils retain their cellular integrity. This provides a clear separation of basophils from other cell types by the impedance and light scatter measurements.

Figure 3A:
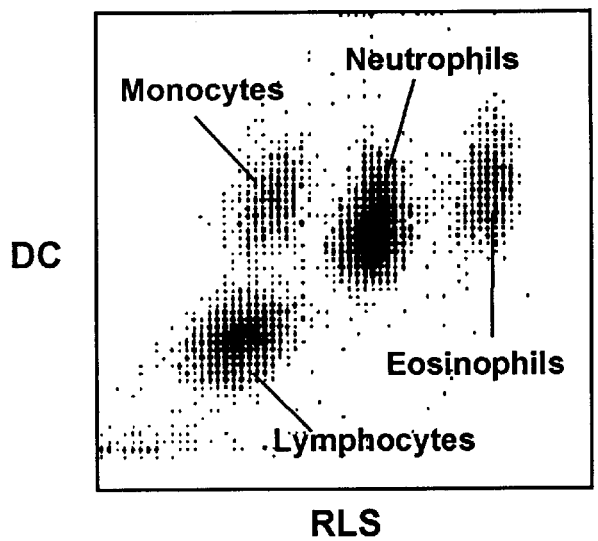
FIGS. 3a, 3b and 3c show a DC vs. RLS, a DC vs. OP, and a RF vs. LS diagrams of a whole blood sample processed as described in Example VI using the lytic reagent described in Example III and the stabilizing reagent described in Example V.

A comparison of leukocyte subpopulation conditions under the treatment of different lytic reagents can be made between FIG. 1a and FIG. 3a. FIG. 3a shows a two dimensional diagram of leukocyte subpopulations obtained by using the second lytic reagent system of the third embodiment of the present invention. In the later case, the impedance and light scatter measurement methods are identical to that described above. However, using the second lytic reagent system, the leukocytes are preserved at near native stage during the measurement. In FIG. 3a, basophils are behind lymphocytes. Upon lysing with the lytic reagent composition of the first embodiment described above, lymphocytes are damaged and moved away. It is apparent from the comparison that it is the selective lysing among different leukocyte subpopulations that provides the separation among them.

Figure 1B:
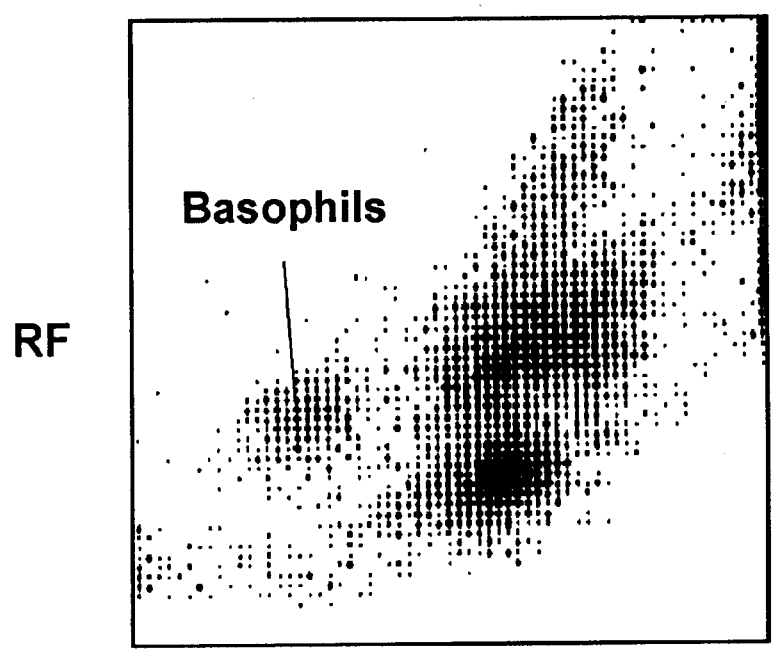

In addition to impedance and light scatter measurements, basophils can also be separated from other cell types by using radio frequency and light scatter measurements. FIG. 1b shows a RF vs. Log LS diagram of the same blood sample shown in FIG. 1a, analyzed as described in Example I.

In a third embodiment of the present invention, a method is provided for lysis of red blood cells in a blood sample and differentiation of leukocytes into at least five subpopulations. The method comprises the steps of: step 1) treating a first aliquot of a blood sample with a first lytic reagent for a time sufficient to lyse red blood cells and selectively lyse leukocyte subpopulations in said blood sample, then inhibiting further lysing reaction by adding a stabilizing reagent, step 2) treating a second aliquot of the blood sample with a second lytic reagent system sufficient to lyse red blood cells and preserve leukocytes in said blood sample, step 3) analyzing the treated first aliquot of the blood sample using impedance and light scatter measurements, or using radio frequency and light scatter measurements to differentiate basophils, step 4) analyzing the treated second aliquot of the blood sample using impedance and light scatter measurements, or using radio frequency and light scatter measurements to differentiate leukocytes into four subpopulations, and step 5) using the results of (3) and (4) to report at least five subpopulations of leukocytes.

Step 1, which treats a first aliquot of blood, is accomplished using the lytic reagent composition of the first embodiment and the stabilizing reagent described in the second embodiment of this invention. Step 3, which is directed to analyzing the first aliquot of the blood sample, is accomplished by the method described in the second embodiment of this invention.

Step 2 is accomplished by treating a second aliquot of the blood sample with a second lytic reagent system sufficient to lyse red blood cells and to preserve leukocytes in the blood sample. Using the second lytic reagent system, leukocytes can be separated into monocytes, eosinophils, neutrophils, and a lymphocyte/basophil cluster by impedance and light scatter measurements, or radio frequency and light scatter measurements. The blood sample is exposed to the second lytic reagent for less than 10 seconds.

The second lytic reagent system typically will include a lytic reagent and a hypertonic, alkaline stabilizing reagent composition. A first example of the second lytic reagent system comprises a lytic reagent comprising an ethoxylated long chain amine compound represented by the general formula:

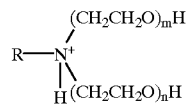

wherein R is an alkyl, alkenyl or alkynyl group having 12 to 22 carbon atoms, m and n are each 1 or more and m+n is between 20 and 40; and an acid to adjust the pH of the lytic reagent to be within the range of 2.0 to 3.6; and a hypertonic, alkaline stabilizing reagent composition. Preferably, R is an alkyl group having 14 to 20 carbon atoms. In addition, it is preferred that the acid used to adjust the pH comprises an organic acid. Most preferably the acid used to adjust the pH is formic acid, or a mixture of formic acid and an acid selected from the group consisting of acetic, citric, oxalic, glycolic, propionic, hydrochloric, sulfuric and phosphoric and mixtures thereof.

A second example of the second lytic reagent system comprises a lytic reagent comprising a polyoxyethylene based surfactant represented by the general formula:

wherein $R_1$ is an alkyl, alkenyl or alkynyl group having 10 to 22 carbon atoms, $R_2$ is —O— or —COO—, and n is between 20 and 35; and an acid to adjust the pH of the lytic reagent composition to be within the range of 2.0 to 4.0, and a hypertonic, alkaline stabilizing reagent composition. Preferably R is an alkyl group having 12 to 20 carbon atoms. In addition, it is preferred that the acid used to adjust the pH comprises an organic acid. Most preferably the acid used to adjust the pH is formic acid, or an effective mixture of formic acid and an acid selected from the group consisting of acetic, citric, oxalic, glycolic, propionic, hydrochloric, sulfuric and phosphoric and mixtures thereof.

Two examples of the lytic reagent of the second lytic reagent system are provided in Examples III and IV. An example of a stabilizing reagent that is used with the lytic reagents of Example III and IV is provided in Example V.

Figure 3B:
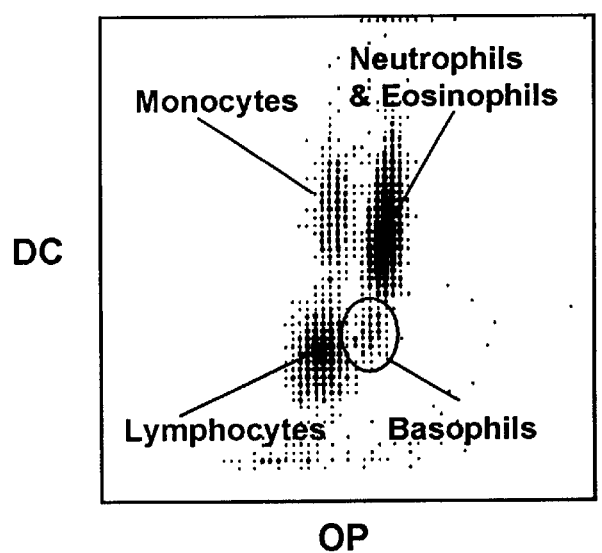
Figure 3C:
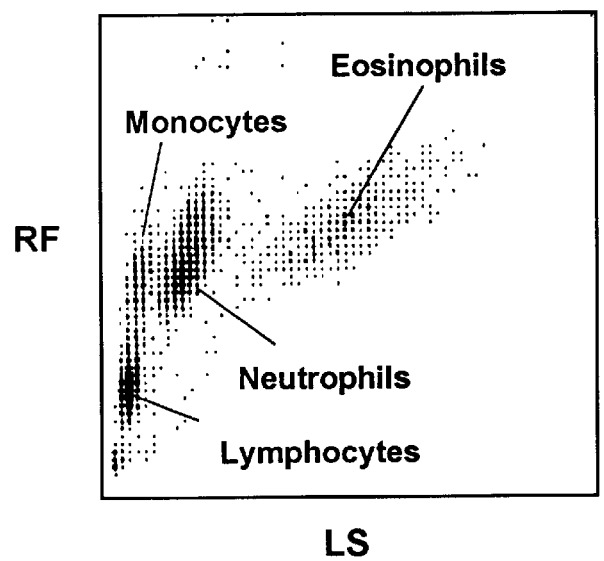

Step 4 is accomplished by analyzing the second aliquot of the blood using impedance and light scatter measurements, or using radio frequency and light scatter measurements. FIGS. 3a and 3c depict the four leukocyte subpopulations that were obtained using the second lytic reagent described in Example III and the stabilizing reagent composition described in Example V from a blood sample analyzed as described in the method of Example VI. As shown in FIGS. 3a and 3c monocytes, neutrophils, eosinophils and a lymphocyte/basophil cluster are clearly separated either using impedance and light scatter measurements, or using radio frequency and light scatter measurements.

Step 5 reports at least five subpopulations of leukocytes. As noted above, the monocytes, neutrophils, and eosinophils are directly obtained in step 4. The lymphocyte subpopulation is obtained by subtracting the basophil subpopulation obtained in step 3 from the sum of the lymphocytes and the basophils obtained in step 4.

In a fourth embodiment, the present invention relates to a third lytic reagent composition and method for differential analysis of eosinophil subpopulation of the leukocytes. The third lytic reagent composition comprises:

(a) a polyoxyethylene based surfactant represented by the general formula:

wherein $R_1$ is an alkyl, alkenyl or alkynyl group having 10 to 22 carbon atoms, $R_2$ is —O— or —COO—, and n is between 20 and 35;

(b) a quaternary ammonium salt, represented by following molecular structure:

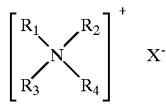

wherein $R_2$, $R_3$ and $R_4$ are alkyl groups having 1 to 4 carbon atoms and $X^-$ is chloride and bromide anions; $R_1$ is an alkyl, alkenyl or alkynyl group having 16 carbon atoms ($C_{16}$); and (c) an acid to adjust pH of the reagent composition from about 1.7 to about 2.3.

The third lytic reagent composition can further comprise a second quaternary ammonium salt wherein $R_1$ is an alkyl, alkenyl or alkynyl group having 14 carbon atoms ($C_{14}$).

Preferably, $R_2$, $R_3$ and $R_4$ are methyl groups, and $R_1$ is a cetyl, or a mixture of cetyl and tetradecyl groups. More preferably, a mixture of cetyltrimethyl ammonium bromide and tetradecyltrimethyl ammonium bromide is used.

The concentration of the polyoxyethylene based surfactant is from about 0.05% to about 6.0% (w/v), preferably from 0.1% to 0.9% (W/V). The concentration of the quaternary ammonium salt is from about 0.08% to about 1.2% (w/v), preferably from about 0.1% to about 0.3% (W/V).

Suitable examples of the acid are phosphoric acid, formic acid, oxalic acid, malonic acid and mixtures thereof. Preferably, the acid is phosphoric acid. The amount of the acid needs to be sufficient for lysing of red blood cells and leukocytes other than eosinophils. The concentration of the acid is from about 0.10% to about 0.5% (W/V). The pH of the lytic reagent is within a range from about 1.7 to about 2.3.

The method of this embodiment comprises the steps of: step 1) exposing a blood sample to the third lytic reagent composition for a time sufficient to lyse red blood cells and leukocytes other than eosinophils, step 2) adding a hypertonic, alkaline stabilizing reagent composition to inhibit further lysing reaction; step 3) differentiating eosinophils from other cell types using one member of the group consisting of (1) impedance and light scatter measurements, (2) impedance and radio frequency measurements, (3) radio frequency and light scatter measurements, (4) impedance measurement, and (5) radio frequency measurement.

The third lytic reagent composition used in step 1 and the stabilizing reagent composition used in step 2 form a lytic reagent system for blood cell sample treatment, which enables the differentiation of eosinophils from other cell types by above described measurements.

The blood sample is exposed to the lytic reagent by mixing with the lytic reagent composition for a time sufficient to lyse red blood cells and leukocytes other than eosinophils in said blood sample. The blood sample is mixed with the lytic reagent composition at room temperature. Preferably the temperature will be between approximately 15 to 30° C. The mixing time is less than 5 seconds, preferably less than 3 seconds.

Figure 2A:
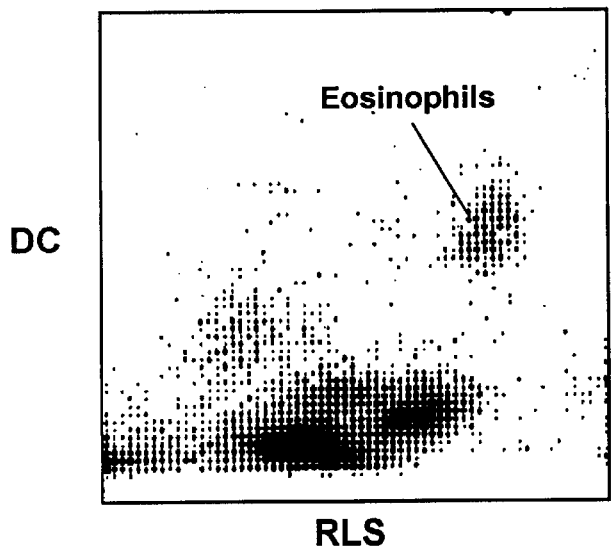
FIGS. 2a, 2b and 2c show a DC vs. RLS, a DC vs. OP (opacity, a function of DC and RF), and a RF vs. LS diagrams of a whole blood sample processed as described in Example II. The diagrams show eosinophil differentiation from other cell types by three different combinations of measurements.

An example of a stabilizing reagent is provided in Example V. Example II illustrates an example using the lytic reagent composition and the method of this embodiment for differential analysis of eosinophils of a whole blood sample. FIG. 2a shows a two dimensional diagram (DC vs. RLS) obtained from a blood sample analyzed as described in Example II. As shown in FIG. 2a, leukocytes other than eosinophils are damaged after treated with the lytic reagent composition. On the contrary, eosinophils remain intact and are separated from other cell types by using impedance and light scatter measurements.

Figure 2B:
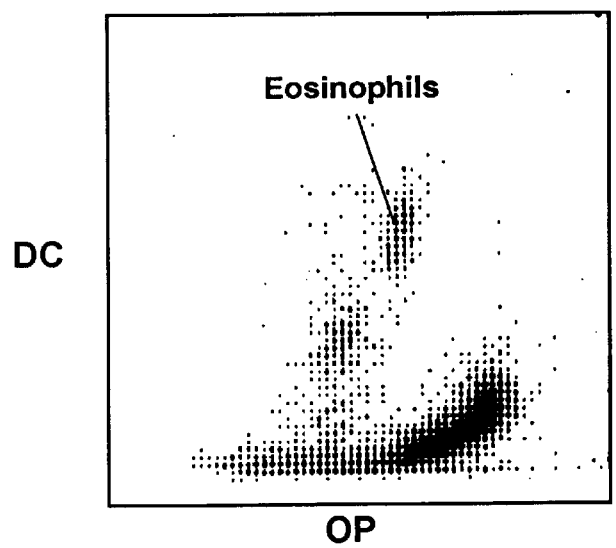
Figure 2C:
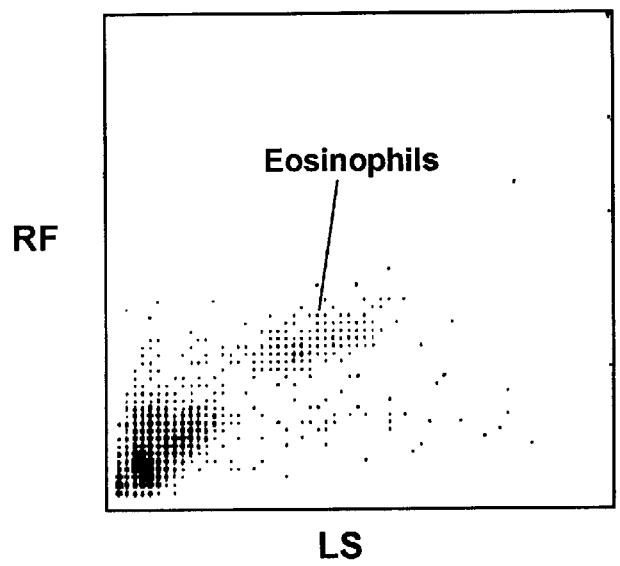

In addition to impedance and light scatter measurements, eosinophils can also be separated from other cell types by using impedance (DC) and radio frequency (RF) measurements, or by using radio frequency and light scatter measurements. FIGS. 2b and 2c show a DC vs. opacity (OP, a function of RF and DC) diagram, and a RF vs. LS diagram, respectively, of the same blood sample shown in FIG. 2a, analyzed as described in Example II. Therefore, with this embodiment, three different combinations of measurements can be used for differential analysis of eosinophils, i.e., impedance and light scatter measurements, impedance and radio frequency measurements, and radio frequency and light scatter measurements. Details of radio frequency measurement principles and techniques are taught in U.S. Pat. Nos. 4,298,836 and 5,125,737 assigned to Coulter Electronics, Inc.

It has been found that with a quaternary ammonium salt having $R_1$ of 16 carbon atoms, the eosinophils are differentiated from other cell types by impedance and light scatter measurements. However, with such a composition, the differentiation from other cell types is not sufficient when the treated blood sample is analyzed by impedance and radio frequency measurements. In the presence of a second quaternary ammonium salt having $R_1$ of 14 carbon atoms, the eosinophils are differentiated from other cell types by any one of the above described three combinations of measurements.

Furthermore, as shown by FIGS. 2a and 2b, eosinophils are clearly separated from other cell types on the DC axis. Also shown by FIG. 2c, eosinophils are separated from other cell types on the RF axis. Therefore, eosinophils of a blood cell sample treated by the lytic reagent system described in this embodiment can also be differentiated by using impedance measurement only, or by using radio frequency measurement only.

In a fifth embodiment, the present invention relates to a method for differentiating leukocytes into at least five subpopulations. The method comprises the steps of: step 1) treating a first aliquot of a blood sample with the lytic reagent composition comprising a polyoxyethylene based surfactant, a mixture of $C_{16}$ and $C_{14}$ quatemary ammonium salt and an acid for a time sufficient to lyse red blood cells and selectively lyse leukocyte subpopulations in the blood sample, then inhibiting further lysing reaction by adding a hypertonic alkaline stabilizing reagent, step 2) treating a second aliquot of the blood sample with a second lytic reagent system sufficient to lyse red blood cells and preserve leukocyte subpopulations in the blood sample, step 3) analyzing the treated first aliquot of the blood sample to differentiate at least one leukocyte subpopulations using one member of the group consisting of (1) impedance and radio frequency measurements, (2) impedance measurement, and (3) radio frequency measurement; step 4) analyzing the treated second aliquot of the blood sample using impedance and radio frequency measurements to differentiate leukocytes into four subpopulations, and step 5) using the results of (3) and (4) to report at least five subpopulations of leukocytes.

As previously discussed in the third embodiment, when a blood sample is treated by the second lytic reagent system of the third embodiment, red blood cells are lysed and leukocytes are preserved for differential analysis. Example VI shows such an example. In this embodiment, a blood sample is treated using the second lytic reagent system and the process of the third embodiment, then is analyzed by impedance and radio frequency measurements. This analysis enables a differentiation of leukocytes into four subpopulations, i.e., monocytes, lymphocytes, basophils and a neutrophil/eosinophil cluster. As shown in FIG. 3b (DC vs. Opacity, a function of DC and RF), neutrophils and eosinophils overlap when measured by impedance and ratio frequency analyses. On the other hand, with the lytic reagent composition of the fourth embodiment, eosinophils are differentiated from other leukocyte subpopulations including neutrophils by impedance and radio frequency measurements, by impedance measurement only, or by radio frequency measurement only. Therefore, by subtracting eosinophils obtained by the method of the fourth embodiment from the sum of neutrophils and eosinophils obtained from the method of this embodiment, one can obtain the count of the neutrophils. Therefore, the method of this embodiment enables a differentiation of leukocytes into five subpopulations.

The lytic reagent compositions for basophil and eosinophil differential analyses, second lytic reagent system, or a combination thereof can each be sold as a kit wherein the lytic reagent composition and the stabilizing composition are each packed in a container, such as a plastic container. Instructions on how to use these components in accordance with the present invention are preferably included inside or on the container.

The invention is further described by reference to the following examples, which are intended to be illustrative and not limiting.

EXAMPLE I

A Lytic Reaaent Composition and Method for Basophil Differentiation

A lytic reagent composition has been formulated with the following composition:

| | |
|---|---|
| 1. Tetradecyltrimethyl ammonium bromide | 2.0 g |
| 2. Plurofac A38 (BASF) | 2.0 g |
| 3. Formic acid | 1.3 ml |
| 4. Deionized water | adjusted to 1 L |

To 28 μl of an EDTA-anti-coagulated normal whole blood sample, 392 μl of the lytic reagent composition was added and the mixture was gently mixed by swirling for about 3 seconds at room temperature (approximately 21° C.). The lysing reaction was retarded by addition of 173 μl of the stabilizing reagent of Example V. The blood mixture was gently mixed and was analyzed about 18 seconds after the addition of the stabilizing reagent. The differential analysis was performed on an experimental hematology analyzer equipped with impedance (DC), light scatter (10°–70°) and radio frequency (RF) detection devices utilizing focused flow technique with a known flow rate. The resulting two-dimensional diagrams are illustrated in FIGS. 1a and 1b. The vertical and horizontal axes are DC and rotated light scatter (RLS) in FIG. 1a, and are RF and Log LS in FIG. 1b, respectively. As shown, the basophil subpopulation is clearly separated from other cell types either using impedance and light scatter measurements, or using radio frequency and light scatter measurements.

EXAMPLE II

A Lytic Reagent Composition and Method for Eosinophil Differentiation

A lytic reagent composition has been formulated with the following composition:

| | |
|---|---|
| 1. Cetyltrimethyl ammonium bromide | 1.2 g |
| 2. Tetradecyltrimethyl ammonium bromide | 0.5 g |
| 3. Plurofac A38 (BASF) | 3.0 g |
| 4. Phosphoric acid | 1.0 ml |
| 5. EDTA | 0.5 g |
| 6. Deionized water | adjusted to 1 L |

To 28 μl of an EDTA-anti-coagulated normal whole blood sample, 392 μl of the lytic reagent composition was added and the mixture was gently mixed by swirling for about 2 seconds at room temperature (approximately 21° C.). The lysing reaction was retarded by the addition of 173 μl the stabilizing reagent of Example V. The blood mixture was gently mixed and was analyzed about 7 seconds after the addition of the stabilizing reagent. The differential analysis was performed on an experimental hematology analyzer equipped with impedance (DC), light scatter (10°–70°) and radio frequency (RF) detection devices utilizing focused flow technique with a known flow rate. The resulting two-dimensional diagrams are illustrated in FIGS. 2a, 2b and 2c. The vertical and horizontal axes are DC and rotated light scatter (RLS) in FIG. 2a, DC and opacity (OP, a function of RF and DC) in FIG. 2b, RF and LS in FIG. 2c respectively. As shown, the eosinophil subpopulation is separated from other cell types in all three diagrams.

EXAMPLE III

First Example of the Lytic Reaaent of the Second Lytic Reaaent System

A lytic reagent composition encompassing the ethoxylated long chain amine compound has been formulated with the following composition:

An ethoxylated long chain amine compound with formula:

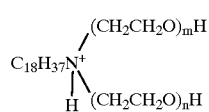

where m+n has a value of 27, was dissolved in deionized water at a concentration of 20 g/L. Formic acid was used to adjust the pH to 3.2. In addition, the following preservatives were added: 0.2 g/L EDTA, 0.5 g/L Dantogard Plus (LONZA), and 0.05 g/L 2,6-Di-tert-butyl4-methylphenol (predissolved in ethanol).

EXAMPLE IV

Second Example of the Lytic Reagent of the Second Lytic Reagent System

A lytic reagent composition encompassing the polyoxyethylene based surfactant has been formulated with the following composition:

A polyoxyethylene based surfactant with formula:

$C_{18}H_{37}O(CH_2CH_2O)_nH$ where n is 30, was dissolved in deionized water at a concentration of 20 g/L. 0.8 g/L of sodium dodecylsulfate (SDS, Aldrich) was added. Formic acid was used to adjust the pH to 2.8.

The lytic reagents of Example III and IV are used in conjunction with a stabilizing reagent to form the second lytic reagent system that lyses red blood cells and preserves the leukocytes for differential analysis. An example of the stabilizing reagent is described in Example V.

EXAMPLE V

Stabilizing Reagent Composition

A stabilizing reagent has been formulated by dissolving 14 g/L of NaCl, 32 g/L of $Na_2SO_4$, and 6.6 g/L of $Na_2CO_3$ buffer in deionized water. The pH of the reagent is about 11.0, and the osmolality is about 1080 mOsm.

EXAMPLE VI

Differentiation of Leukocyte Subpopulations of a Blood Sample

To 34 μl of an EDTA-anti-coagulated normal whole blood sample, 556 μl of the lytic reagent composition of Example III was added and the mixture was gently mixed by swirling for 4 seconds at room temperature (approximately 21° C.). The lysing reaction was retarded by the addition 240 μl of the stabilizing reagent of Example V. The blood mixture was gently mixed and was ready for differential analysis about 10 seconds after the addition of the stabilizing reagent. The differential analysis was performed on an experimental hematology analyzer equipped with impedance (DC), light scatter (10°–70°) and radio frequency (RF) detection devices utilizing focused flow technique. FIGS. 3a, 3b and 3c show a DC vs. RLS diagram, a DC vs. opacity (OP, a function of RF and DC) diagram of the analysis, and a RF vs. LS diagram, respectively. As shown in FIGS. 3a and 3c four leukocyte subpopulations, monocytes, neutrophils, eosinophils, and a lymphocyte/basophil cluster, are clearly separated either by impedance and light scatter measurements, or by radio frequency and light scatter measurements. In FIG. 3b, different four leukocyte subpopulations are separated by the impedance and radio frequency measurements, i.e., monocytes, lymphocytes, basophils and a neutrophil/eosinophil cluster.

While certain representative embodiments and details have been shown for the purpose of illustrating the invention, various changes and modifications can be made therein without departing from the scope of the invention as defined in the appended claims.

What is claimed is:

1. A lytic reagent composition comprising:

(a) a polyoxyethylene based surfactant represented by the general formula:

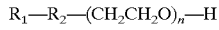

wherein $R_1$ is an alkyl, alkenyl or alkynyl group having 10 to 22 carbon atoms, $R_2$ is —O— or —COO—, and n is between 20 and 35;

(b) a quaternary ammonium salt, represented by following molecular structure:

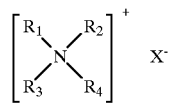

wherein $R_1$ is an alkyl, alkenyl or alkynyl group having 14 carbon atoms; $R_2$, $R_3$ and $R_4$ are alkyl groups having 1 to 4 carbon atoms and $X^-$ is chloride or bromide anions; and (c) an acid to adjust pH of the reagent composition from about 1.7 to about 2.4.

2. The lytic reagent composition of claim 1, wherein said quaternary ammonium salt is tetradecyltrimethyl ammonium bromide.

3. The lytic reagent composition of claim 1, wherein said quaternary ammonium salt is at a concentration from about 0.15% to about 0.4% (W/V).

4. The lytic reagent composition of claim 1, wherein said polyoxyethylene based surfactant is at a concentration from about 0.05% to about 0.8% (W/V).

5. The lytic reagent composition of claim 1, wherein said acid comprises an organic acid, an inorganic acid, and mixtures thereof.

6. The lytic reagent composition of claim 5, wherein said acid is selected from the group consisting of formic acid, citric acid, oxalic acid, malonic acid, phosphoric acid, and mixtures thereof.

7. The lytic reagent composition of claim 5, wherein concentration of said acid is from about 0.1% to about 0.3% (W/V).

8. A method for analysis of leukocyte subpopulations comprising:

(a) exposing a blood sample to a lytic reagent composition of claim 1 for a time sufficient to lyse red blood cells and selectively lyse leukocyte subpopulations except basophils in said blood sample;

(b) adding a hypertonic alkaline stabilizing reagent composition to said blood sample, wherein said stabilizing reagent composition inhibits further lytic action; and (c) analyzing said blood sample to differentiate basophils from other cell types using an automated analyzer.

9. The method of claim 8, wherein lysing of the red blood cells and differentiating basophils in said blood sample is at room temperature.

10. The method of claim 8, wherein said analyzing is performed by using impedance and light scatter measurements.

11. The method of claim 8, wherein said analyzing is performed by using radio frequency and light scatter measurements.

12. A method for lysis of red blood cells in a blood sample and differentiation of leukocyte subpopulations comprising;

(a) treating a first aliquot of a blood sample with the lytic reagent composition of claim 1 for a time sufficient to lyse red blood cells and selectively lyse leukocyte subpopulations except basophils in said blood sample, then inhibiting further lytic reaction by adding a hypertonic alkaline stabilizing reagent to the blood sample;

(b) treating a second aliquot of said blood sample with a second lytic reagent system sufficient to lyse red blood cells and preserve leukocytes in said blood sample;

(c) analyzing the treated first aliquot of said blood sample to differentiate basophils using one member of the group consisting of (1) impedance and light scatter measurements, and (2) radio frequency and light scatter measurements;
(d) analyzing the treated second aliquot of said blood sample to differentiate leukocytes into four types comprising monocytes, neutrophils, eosinophils, and sum of lymphocytes and basophils using one member of the group consisting of (1) impedance and light scatter measurements, and (2) radio frequency and light scatter measurements; and
(e) using the results of (c) and (d) to report at least five subpopulations of leukocytes.

13. A lytic reagent system, comprising:
(1) a lytic reagent composition comprising:
(a) a polyoxyethylene based surfactant represented by the general formula:

wherein $R_1$ is an alkyl, alkenyl or alkynyl group having 10 to 22 carbon atoms, $R_2$ is —O— or —COO—, and n is between 20 and 35;
(b) a quaternary ammonium salt, represented by following molecular structure:

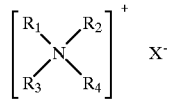

wherein $R_1$ is an alkyl, alkenyl or alkynyl group having 14 carbon atoms; $R_2$, $R_3$ and $R_4$ are alkyl groups having 1 to 4 carbon atoms and $X^-$ is chloride or bromide anions; and
(c) an acid to adjust pH of the reagent composition from about 1.7 to about 2.4, and
(2) a hypertonic, alkaline stabilizing reagent composition.

14. A lytic reagent composition comprising:
(a) a polyoxyethylene based surfactant represented by the general formula:

wherein $R_1$ is an alkyl, alkenyl or alkynyl group having 10 to 22 carbon atoms, $R_2$ is —O— or —COO—, and n is between 20 and 35;
(b) a quaternary ammonium salt, represented by following molecular structure:

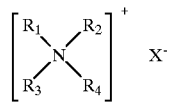

wherein $R_1$ is an alkyl, alkenyl or alkynyl group having 16 carbon atoms; $R_2$, $R_3$ and $R_4$ are alkyl groups having 1 to 4 carbon atoms and $X^-$ is chloride or bromide anions; and
(c) an acid to adjust pH of the reagent composition from about 1.7 to about 2.3.

15. The lytic reagent composition of claim 14, wherein said quaternary ammonium salt is cetyltrimethyl ammonium bromide.

16. The lytic reagent composition of claim 14, wherein the composition further comprises a second quaternary ammonium salt, represented by following molecular structure:

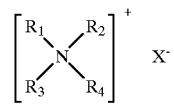

wherein $R_1$ is an alkyl, alkenyl or alkynyl group having 14 carbon atoms; $R_2$, $R_3$ and $R_4$ are alkyl groups having 1 to 4 carbon atoms and $X^-$ is chloride or bromide anions.

17. The lytic reagent composition of claim 16, wherein the second quaternary ammonium salt is tetradecyltrimethyl ammonium bromide.

18. The lytic reagent composition of claim 16, wherein said quaternary ammonium salts are at a concentration from about 0.08% to bout 1.2% (W/V).

19. A method for analysis of leukocyte subpopulations comprising:
(a) exposing a blood sample to a lytic reagent composition of claim 16 for a time sufficient to lyse red blood cells and selectively lyse leukocyte subpopulations except eosinophils in said blood sample;
(b) adding a hypertonic alkaline stabilizing reagent composition to said exposed blood sample, wherein said stabilizing reagent composition inhibits further lytic action; and
(c) analyzing said blood sample to differentiate eosinophils from other cell types using an automated analyzer.

20. The method of claim 19, wherein lysing of the red blood cells and differentiating eosinophils in said blood sample is at room temperature.

21. The method of claim 19, wherein said analyzing is performed by using impedance and light scatter measurements.

22. The method of claim 19, wherein said analyzing is performed by using impedance and radio frequency measurements.

23. The method of claim 19, wherein said analyzing is performed by using radio frequency and light scatter measurements.

24. The method of claim 19, wherein said analyzing is performed by using impedance measurement.

25. The method of claim 19, wherein said analyzing is performed by using radio frequency measurement.

26. A method for lysis of red blood cells in a blood sample and differentiation of leukocyte subpopulations comprising:
(a) treating a first aliquot of a blood sample with the lytic reagent composition of claim 16 for a time sufficient to lyse red blood cells and selectively lyse leukocyte subpopulations except eosinophils in said blood sample, then inhibiting further lytic reaction by adding a hypertonic alkaline stabilizing reagent to the blood sample;
(b) treating a second aliquot of said blood sample with a second lytic reagent system sufficient to lyse red blood cells and preserve leukocytes in said blood sample;
(c) analyzing the treated first aliquot of said blood sample to differentiate eosinophils using one member of the group consisting of (1) impedance and radio frequency measurements, (2) impedance measurement, and (3) radio frequency measurement;
(d) analyzing the treated second aliquot of said blood sample to differentiate leukocytes into four types comprising monocytes, lymphocytes, basophils, and the sum of neutrophils and eosinophils using impedance and radio frequency measurements; and (e) using the results of (c) and (d) to report at least five subpopulations of leukocytes.

27. The method of any one of claim 12 or 26 wherein the second lytic reagent system comprises:
    (a) a lytic reagent comprising an ethoxylated long chain amine compound represented by the general formula:

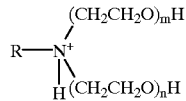

wherein R is an alkyl, alkenyl or alkynyl group having 12 to 22 carbon atoms, m and n are each 1 or more and m+n is between 20 and 40; and an acid to adjust the pH of the lytic reagent to be within the range of 2.0 to 3.6; and
    (b) a hypertonic, alkaline stabilizing reagent composition.

28. The method of any one of claim 12 or, 26 wherein the second lytic reagent system comprises:
    (a) a lytic reagent comprising a polyoxyethylene based surfactant for the determination of at least four leukocyte subpopulations in a blood sample represented by the general formula:

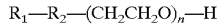

wherein $R_1$ is an alkyl, alkenyl or alkynyl group having 10 to 22 carbon atoms, $R_2$ is —O— or —COO—, and n is between 20 and 35; and an acid to adjust the pH of the lytic reagent to be within the range of 2.0 to 4.0; and
    (b) a hypertonic, alkaline stabilizing reagent composition.

29. The lytic reagent composition of claim 14, wherein said polyoxyethylene based surfactant is at a concentration from about 0.05% to about 6.0% (W/V).

30. The lytic reagent composition of claim 14, wherein said acid comprises an organic acid, an inorganic acid, and mixtures thereof.

31. The lytic reagent composition of claim 14, wherein said acid is selected from the group consisting of phosphoric acid, formic acid, malonic acid, oxalic acid, and mixtures thereof.

32. The lytic reagent composition of claim 14, wherein said acid is phosphoric acid.

33. The lytic reagent composition of claim 14, wherein concentration of said acid is from about 0.1% to 0.5% (W/V).

34. A lytic reagent system, comprising:
    (1) a lytic reagent composition comprising:
        (a) a polyoxyethylene based surfactant represented by the general formula:

wherein $R_1$ is an alkyl, alkenyl or alkynyl group having 10 to 22 carbon atoms, $R_2$ is —O— or —COO—, and n is between 20 and 35;
        (b) a quaternary ammonium salt, represented by following molecular structure:

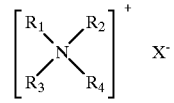

wherein $R_1$ is an alkyl, alkenyl or alkynyl group having 16 carbon atoms; $R_2$, $R_3$ and $R_4$ are alkyl groups having 1 to 4 carbon atoms and $X^-$ is chloride or bromide anions; and
        (c) an acid to adjust pH of the reagent composition from about 1.7 to about 2.3, and
    (2) a hypertonic, alkaline stabilizing reagent composition.

35. The lytic reagent system of claim 34, wherein the lytic reagent composition further comprises a second quaternary ammonium salt, represented by following molecular structure:

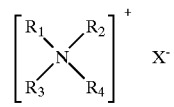

wherein $R_1$ is an alkyl, alkenyl or alkynyl group having 14 carbon atoms; $R_2$, $R_3$ and $R_4$ are alkyl groups having 1 to 4 carbon atoms and $X^-$ is chloride or bromide anions.

36. The lytic reagent composition of claim 35, wherein the second quaternary ammonium salt is tetradecyltrimethyl ammonium bromide.

* * * * *